United States Patent [19]
Maryanoff et al.

[11] Patent Number: 5,387,700
[45] Date of Patent: Feb. 7, 1995

[54] PROCESS FOR THE PREPARATION OF CHLOROSULFATE AND SULFAMATE DERIVATIVES OF 2,3:4,5-BIS-O-(1-METHYLETHYLIDENE)-β-D-FRUCTOPYRANOSE AND (1-METHYLCYCLOHEXYL)METHANOL

[75] Inventors: Cynthia A. Maryanoff, New Hope; Lorraine Scott, North Wales; Kirk L. Sorgi, Blue Bell, all of Pa.

[73] Assignee: McNeilab, Inc., Spring House, Pa.

[21] Appl. No.: 106,470

[22] Filed: Aug. 12, 1993

Related U.S. Application Data

[63] Continuation-in-part of Ser. No. 926,269, Aug. 5, 1992, abandoned, which is a continuation-in-part of Ser. No. 762,720, Sep. 19, 1991, abandoned.

[51] Int. Cl.$^6$ ............... C07D 311/78; C07D 311/94; C07D 309/06; C07C 309/02
[52] U.S. Cl. .................... 549/387; 549/336; 549/337; 549/396; 549/426; 549/427; 549/433; 549/443; 558/48
[58] Field of Search ............... 549/387, 396, 426, 427, 549/336, 337, 433, 443; 558/48

[56] References Cited

U.S. PATENT DOCUMENTS 4,582,916  4/1986  Maryanoff et al. ............... 549/387

Primary Examiner—Nicky Chan

[57] ABSTRACT

A process for producing chlorosulfate and sulfamate esters of 2,3:4,5-bis-O-(1-methylethylidene)-β-D-fructopyranose and (1-methylcyclohexyl)methanol is disclosed. The process involves a two step procedure involving in the first step reacting of an alcohol with sulfuryl chloride in the presence of a tertiary or heterocyclic amine base in a solvent selected from the group consisting of toluene, t-butyl methyl ether or tetrahydrofuran to produce a chlorosulfate intermediate, which is preferably stabilized by an aqueous wash and/or treatment with a base, and in the second step reacting of the resulting intermediate with an amine in a solvent selected from the group consisting of t-butyl methyl ether, tetrahydrofuran and lower alkanol.

28 Claims, No Drawings

PROCESS FOR THE PREPARATION OF CHLOROSULFATE AND SULFAMATE DERIVATIVES OF 2,3:4,5-BIS-O-(1-METHYLETHYLIDENE)-β-D-FRUCTOPYRANOSE AND (1-METHYLCYCLOHEXYL)METHANOL

This application is a continuation-in-part of U.S. Ser. No. 926,269 filed Aug. 5, 1992, now abandoned, which in turn is a continuation-in-part of U.S. Ser. No. 762,720 filed Sep. 19, 1991, now abandoned, the entire disclosure of these applications are hereby incorporated herein by reference.

FIELD OF THE INVENTION

This invention is directed to a process for producing chlorosulfate and sulfamate esters of 2,3:4,5-bis-O-(1-methylethylidene)-β-D-fructopyranose and (1-methylcyclohexyl)methanol. The process in particular is a two step procedure involving in the first step reacting an alcohol with sulfuryl chloride in the presence of a tertiary or heterocyclic amine base in a solvent selected from the group consisting of toluene, t-butyl methyl ether or tetrahydrofuran to produce a chlorosulfate intermediate, and in the second step reacting the resulting intermediate with an amine in a solvent selected from the group consisting of t-butyl methyl ether, tetrahydrofuran and lower alkanol.

BACKGROUND OF THE INVENTION

Sulfamates of the formula I:

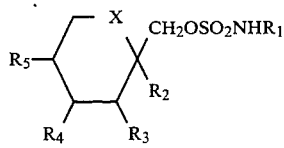

wherein X is O or $CH_2$ and $R_1$, $R_2$, $R_3$, $R_4$, and $R_5$ are as herein defined, are known compounds that have been found to exhibit anticonvulsant activity and thus are useful in the treatment of conditions such as epilepsy. These compounds are disclosed in U.S. Pat. Nos. 4,582,916 and 4,513,006, which also disclose processes for production of such compounds. The entire disclosure of these two patents are hereby incorporated herein by reference.

One reaction scheme disclosed in these prior art patents covers the reaction of an alcohol of the formula $RCH_2OH$ with a chlorosulfamate of the formula $ClSO_2NH_2$ or $ClSO_2NHR_1$ in the presence of a base such as potassium t-butoxide or sodium hydride (NaH) at a temperature of about −20° C. to 25° C. and in a solvent such as toluene, tetrahydrofuran (THF) or dimethylformamide (DMF), wherein R is a moiety of the formula II:

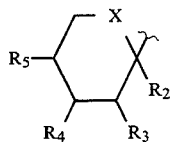

This process has two major disadvantages. One disadvantage is that it calls for a combination of NaH and DMF which has an uncontrollable exotherm and is therefore potentially explosive. See J. Buckley et al., Chemical & Engineering News, Jul. 12, 1982, page 5; and G. DeWail, Chemical & Engineering News, Sep. 13, 1982. Another disadvantage is that the process also uses highly toxic and corrosive chlorosulfonyl isocyanate (CSI) to prepare the commercially unavailable sulfamyl chloride ($ClSO_2NH_2$). The CSI is not only difficult to work with, because of its toxicity and corrosiveness, but also is available front only one commercial supplier.

Another known process disclosed in the above mentioned U.S. Pat. No. 4,513,006 for producing the compounds of formula I comprises the reaction of an alcohol of the formula $RCH_2OH$ with sulfuryl chloride of the formula $SO_2Cl_2$ in the presence of a base such as triethylamine or pyridine at a temperature of about −40° C. to 25° C. in a diethyl ether or methylene chloride solvent to produce a chlorosulfate of the formula $RCH_2OSO_2Cl$. The chlorosulfate of the formula $RCH_2OSO_2Cl$ may then be reacted with an amine of the formula $R_1NH_2$ at a temperature of about −40° C. to 25° C. in a methylene chloride or acetonitrile solvent to produce the compound of the formula I. This process (utilizing diethyl ether, methylene chloride and acetonitrile solvents) produces relatively low yields of the desired end product of formula I in comparison with the process of the present invention.

The final process disclosed in the two patents comprises the reaction of the chlorosulfate of formula $RCH_2OSO_2Cl$ formed as described previously with a metal azide such as sodium azide in a solvent such as methylene chloride or acetonitrile to yield an azidosulfate of the formula $RCH_2OSO_2N_3$. The azidosulfate is then reduced to a compound of the formula I wherein $R_1$ is hydrogen, by catalytic hydrogenation. The disadvantage with this process is that explosions may occur when handling the azide compounds. Also the process contains an additional chemical transformation involving the reduction of the azide to the $NH_2$ moiety.

It is an object of the present invention to provide a new and improved process for producing compounds of the formula I, which uses readily available materials, can be carried out under safe conditions and at relatively high yields. The advantages of the present invention are described in part below and in part will be obvious from this description and by comparison to the prior art processes described in the Examples section below.

SUMMARY OF THE INVENTION

According to the present invention, compounds of the formula 1:

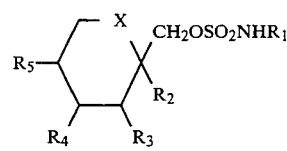

wherein X is O or $CH_2$ and $R_1$, $R_2$, $R_3$, $R_4$ and $R_5$ are as hereinafter defined are synthesized in two steps by reacting an alcohol of the formula $RCH_2OH$, wherein R is a moiety of the formula II:

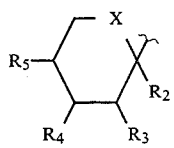

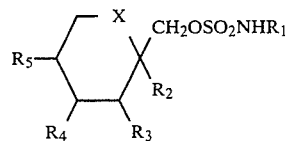

with sulfuryl chloride, in the presence of a base, preferably a tertiary or heterocyclic amine, in a solvent selected from the group consisting of toluene, t-butyl methyl ether (TBME) or tetrahydrofuran (THF), preferably toluene to form a chlorosulfate intermediate compound of the formula $RCH_2OSO_2Cl$ (formula III), and thereafter in a second step reacting the compound of formula III with an amine of the formula $R_1NH_2$, preferably ammonia, in a solvent selected from the group consisting of THF, TBME, and lower alkanol (e.g. methanol or ethanol), preferably tetrahydrofuran to produce the compound of formula I:

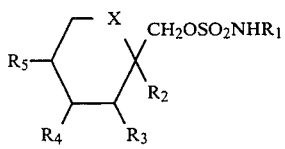

In a preferred embodiment of the process of the invention the chlorosulfate intermediate is stabilized by removing residual acidity by aqueous wash of the product or by treatment with a base such as sodium bicarbonate or more preferably by both treatment with a base and aqueous wash.

It is to be understood that both the foregoing general and the following detailed description are exemplary and explanatory only and are not intended to be restrictive of the invention as claimed.

DETAILED DESCRIPTION OF THE INVENTION

Reference will now be made in detail to particularly preferred embodiments of the invention. Examples of the preferred embodiments are illustrated in the following Examples section.

The novel process of the invention is inherently much safer than the prior art process which employs the potentially explosive combination of NaH/DMF. It also uses sulfuryl chloride and ammonia instead of the highly toxic and corrosive chlorosulfonyl isocyanate (CSI). Further the sulfuryl chloride is more commercially accessible and much less costly than CSI. Moreover, the process results in relatively high yields of about 85% to 97%, as compared with the prior art processes which have yields in the range of from about 1% to 60%. The apparent reason for the high yields are the particularly selected solvents chosen for each step of the reaction sequence and the stabilization of the intermediate chlorosulfate by aqueous wash and/or treatment with a base prior to its reaction with an amine. The combination of the use of inexpensive and readily accessible sulfuryl chloride and the higher yields of purer product results in a much more economical and/or safer process when compared to the prior art processes.

More particularly, the present invention is directed to a process for synthesizing compounds of the formula I:

wherein X is $CH_2$ or O;

$R_1$ is hydrogen or $C_1$–$C_4$ alkyl; and $R_2$, $R_3$, $R_4$ and $R_5$ are independently hydrogen or alkyl, and, when X is O, $R_2$ and $R_3$ and/or $R_4$ and $R_5$, together, may be a methylenedioxy group the following formula IV:

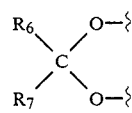

wherein $R_6$ and $R_7$ are the same or different and are hydrogen, alkyl or are both alkyl and joined to form a cyclopentyl or cyclohexyl ring, with the proviso that $R_6$ and $R_7$ may not both be hydrogen at the same time.

$R_1$ in particular is hydrogen or alkyl of about 1 to 4 carbons, such as methyl, ethyl and isopropyl. Alkyl groups for $R_2$, $R_3$, $R_4$, $R_5$, $R_6$ and $R_7$ are of 1 to 3 carbons and include methyl, ethyl, isopropyl and n-propyl. Alkyl throughout this specification includes straight and branched chain alkyl groups.

This process is particularly useful for producing compounds of the formula I wherein X is oxygen and both $R_2$ and $R_3$, and $R_4$ and $R_5$ together are methylenedioxy groups of the formula IV, wherein $R_6$ an $R_7$ are both alkyl.

The process comprises reacting an alcohol of the formula $RCH_2OH$ with sulfuryl chloride of the formula $SO_2Cl_2$ in the presence of a tertiary or heterocyclic amine base such as pyridine, pyridine derivatives or triethylamine, preferably pyridine at a temperature of about $-78°$ C. to 40° C., more preferably at a temperature of about 0° C. to 40° C. in a solvent such as toluene, t-butyl methyl ether (TBME), or tetrahydrofuran (THF), preferably toluene, to produce a chlorosulfate of the formula III, i.e. $RCH_2OSO_2Cl$, wherein R is a moiety of the formula II:

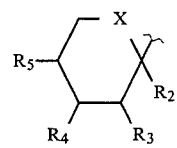

The chlorosulfate of the formula III $RCH_2OSO_2Cl$ is stabilized by aqueous wash from the product mixture or by treatment with a base such as sodium bicarbonate, or preferably by aqueous wash and treatment with a base. The stabilized chlorosulfate intermediate is then reacted with an amine of the formula $R_1NH_2$ at a temperature of about $-50°$ C. to 50° C., more preferably of about 15° C. to 20° C. in a solvent such as THF, TBME, methanol or ethanol, preferably THF to produce a compound of formula I.

The reaction with the amine of the formula $R_1NH_2$ can be carried out using any appropriate amine source, preferably ammonia gas ($R_1$=H) from an ammonia gas generating source such as aqueous or anhydrous ammonia under pressure of from about atmospheric to 50 psi, more preferably at about 20–30 psi, or the amine can be bubbled into the reaction solution. The reaction can also be carried out using a pre-saturated solution of ammonia in THF.

To obtain a purer product the compound of formula I may be recrystallized by conventional techniques such as from ethanol/water or ethyl acetate/hexane.

The starting materials of the formula $RCH_2OH$ may be obtained commercially from Aldrich Chemical Corporation or synthesized by techniques well known in the art. For example, starting materials of the formula $RCH_2OH$, wherein $R_2$, $R_3$, $R_4$ and $R_5$ are methylenedioxy groups of the formula IV may be obtained by the method of R. F. Brady in "Carbohydrate Research", 1970,15, p. 35–40 or by reaction of the trimethylsilyl enol ether of a $R_6COR_7$ ketone or aldehyde with fructose at a temperature of about 25° C. in a solvent such as an alkyl halide, e.g. methylene chloride in the presence of a protic acid such as hydrochloric acid or a Lewis Acid such as zinc chloride. The trimethylsilyl enol ether reaction is described by G. L. Larson et al in *J. Org. Chem.*, 1973,38, No. 22, p. 3935.

A particularly preferred process according to the present invention comprises reacting a compound of the formula V:

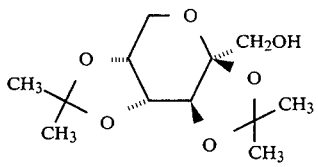

with sulfuryl chloride of the formula $SO_2Cl_2$ in the presence of an amine base, preferably pyridine and in toluene at a temperature of about 0° C. to 4° C. and a pressure of about atmospheric to produce a compound of the formula VI:

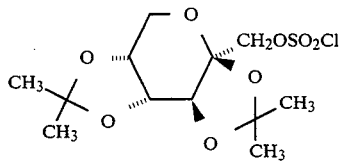

The compound of formula VI is thereafter reacted with ammonia at a pressure of ca. 30 psi in THF at a temperature of about 15° to 20° C. to produce the compound of the formula VII:

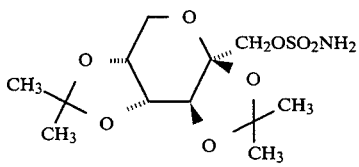

The two-step process of the invention involves (1) the generation of a chlorosulfate VI, followed by (2) treatment with ammonia to generate the sulfamate ester VII. The generation of chlorosulfates using sulfuryl chloride and pyridine is known, however, some sugar derived chlorosulphates have been shown to further react to form chlorinated by-products. See Jennings, H. J. et. al. Can. J. Chem. 1965, 43, 2372, and 3018. Jennings et. al. demonstrated that treatment of methyl-D-glucopyranoside 1 with sulfuryl chloride and pyridine at 0° C. gave the 6-chloro-glucopyranoside 2 as the sole isolated product.

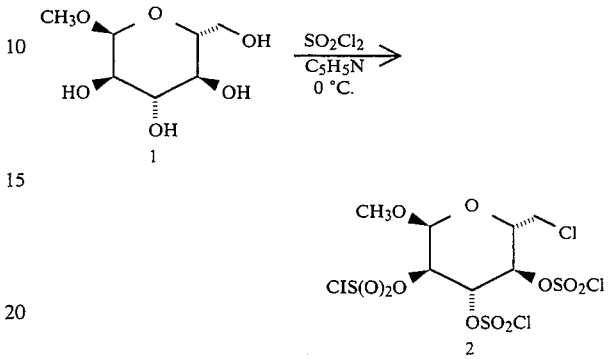

Using the experimental conditions of the present inventive process for preparing chlorosulfate VI, there is no indication of similar chemistry taking place. In light of Jenning's work, the preparation and isolation of high yields of chlorosulfate VI in accordance with the present invention is unexpected.

It is further a surprising discovery that ammonia gas may be used as the amine source in the second reaction step of the process. Prior studies of reaction of chlorosulfates with ammonia indicate production of mixtures of N-alkylated products. See e.g. Buncel E., Chemical Reviews, 1970, 70, No. 3, Pp. 323–337 and Kinkead S. A. et. al. J. Am. Chem. Soc., 1984, 106, 7496. The production of higher yields of pure products from the present process utilizing ammonia gas as the amine source is favorably surprising. The reaction of chlorosulfates with ammonia to generate sulfamates is not well understood and often leads to mixtures of N-alkylated products. Alkyl chlorosulfates can follow three reaction pathways when treated with a nucleophile such as an amine (shown below). Pathway "a" results in C—O bond cleavage to afford an alkylated product, while pathways "b" and "c" result in reaction at sulfur followed by S—O and S—Cl bond cleavages respectively. The pathway chosen is dependent on both the structural properties of the chlorosulfate and nucleophilic amine used.

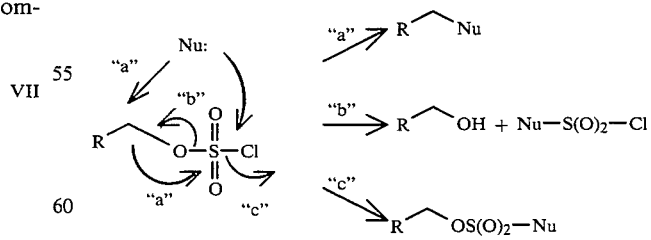

Chlorosulfates prepared from primary alcohols tend to follow the alkylation pathway "a" when ammonia is employed as the nucleophilic amine, however, when the amine is alkylated, such as ethyl amine the pathway chosen tends to be "c". This is best illustrated with the reaction of ethyl chlorosulfate and ammonia. Reaction of ethyl chlorosulfate and ammonia yields mono-, di-, and triethylamine, the products of C—O cleavage (pathway "a"). Also found in the reaction mixture are the alkylated sulfamates 3a and 3b; the products from pathway "c" involving "in situ" generated ethyl- and diethylamine. This demonstrates that ammonia reacts at carbon (pathway "a") and not sulfur, while ethyl- and diethylamine do react at sulfur and cleave the S—Cl bond (pathway "c"). None of sulfamate 4, the product of ammonia displacement (pathway "c") was observed. Considering the tendency of ammonia to react at carbon via pathway "a", it is unexpected that sulfamate VII would be the major product formed from the reaction involving chlorosulfate VI and ammonia.

actually utilized in the experimental section thereof. Advantageously, the reaction conditions for the two step process of the present invention leads to unexpectedly cleaner product in higher yields than that obtained by Maryanoff and Gardocki. The present two step inventive process involves the distinctive improvements of an extractive work-up and isolation to stabilize the chlorosulfate intermediate and the use of particular solvents to achieve its superior results.

The same process can be used to make the L-fructopyranose derived enantiomer instead of the D-fructopyranose enantiomer of formula VII by using the L-enantiomer starting material instead of the D-enantiomer starting material of formula V.

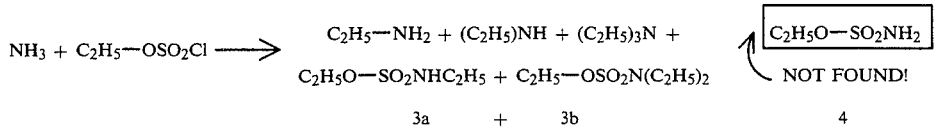

Kochetkov et al, J. Gen. Chem. USSR 1971, 41, 1874 compares the reaction products of ammonia or diethyl amine with the galactopyranose chlorosulfate 5 (an analog of the chlorosulfate VI) and found they react quite differently. With ammonia as the amine source the only identified product was the sulfamate dimer 6, while no sulfamate 8 was produced. In contrast, when 5 is reacted with diethyl amine the only product isolated was the N,N-diethyl sulfamate 7.

The invention will now be illustrated by examples. The examples are not intended to be limiting of the scope of the present invention but read in conjunction with the detailed and general description above, provide further understanding of the present invention and outline a method of practicing the process of the invention.

EXAMPLES

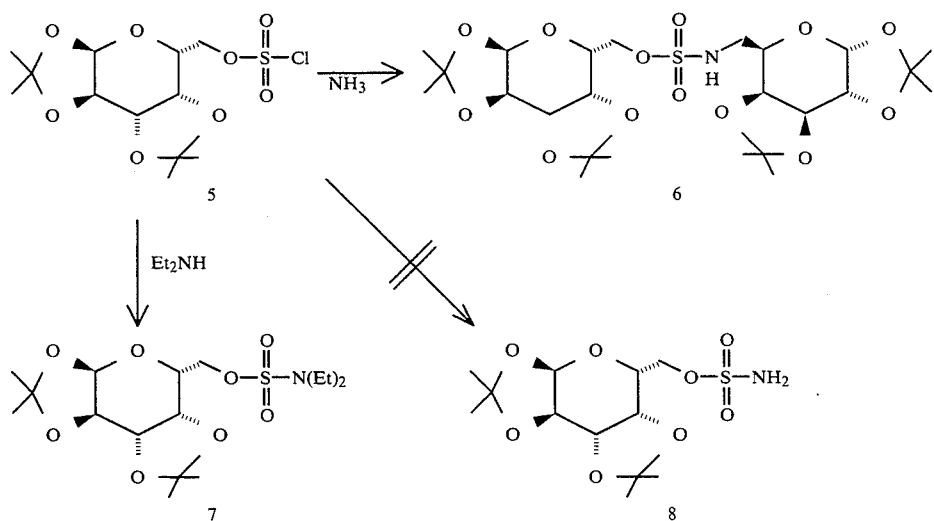

In summary, the overall high yield of sulfamates for the two step process of the invention is unexpected, in light of teaching by prior art. Contrary to the prior art teachings, in the present invention (1) sulfuryl chloride and pyridine react with primary alcohols V to afford the desired chlorosulfates VI, in high purity and yield and (2) ammonia reacts at sulfur and not carbon at chlorosulfates VI to generate the desired sulfamates VII.

Maryanoff and Gardocki in U.S. Pat. No. 4,582,916 report that chlorosulfates (VI) may be reacted with monosubstituted amines (i.e.; $R_1NH_2$) at temperatures of $-40$ to 25 degrees C in solvents like methylene chloride or acetonitrile to produce N-alkylated sulfamates. This patent discloses the preparation of sulfamates using chlorosulfates and amines; the specific use of ammonia as the amine to prepare sulfamate VII is not, however, Examples 1 and 2 show the production of intermediates according to the present invention. Example 3–5 are examples of the production of the final desired sulfamate (VII) product by the two step process of the invention. Examples 6–10 are prior art comparative examples for preparing VII following the conditions described by Maryanoff B. E. et. al. in U.S. Pat. No. 4,582,916. Table 1 compares the yields of the prior art processes of examples 6–10 with the yields of the two step processes of the present invention (Examples 3–5) for producing the compound of formula VII.

Table 2 compares the yields of the process of the present invention (Example 14) with the yields of prior art processes (Examples 11–13) for producing (1- methylcyclohexyl)methane sulfamate. As is apparent from the Tables 1 and 2 the process of the present invention results in yields of final product greatly in excess of the yields of the prior art processes and superior purity of the final product.

−15° C.). The resulting slurry was centrifuged to remove the precipitated salt (sodium sulfate). Solvent was removed from the filtrate by vacuum distillation and the residual oil was stored at room temperature. The semi-solid reaction product was dissolved in t-butyl methyl

TABLE 1

Comparison of Present Invention (Ex. 3–5) vs. Prior Art Process (Ex. 6–10) for Preparing Sulfamate VII

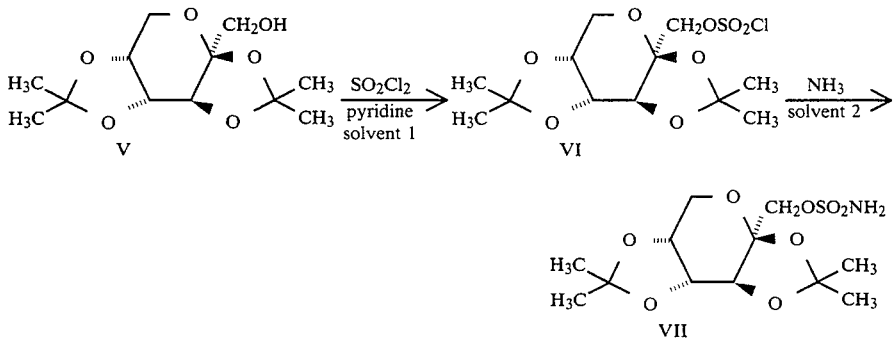

| Process | solvent 1 | solvent 2 | $NH_3$ | Phys. Descript (VII) | Purity (%) (VII) | Yield # (VII) |
|---|---|---|---|---|---|---|
| Ex. 3 | toluene | THF | 30 psi | wh. solid | 99.70 | 93.50 |
| Ex. 4 | toluene | THF | bubbling | wh. solid | 96.20 | 87.20 |
| Ex. 5 | toluene | THF | saturation | wh. solid | — | 83.30* |
| Ex. 6 | $CH_2Cl_2$ | $CH_2Cl_2$ | bubbling | bl.tar | 15.10 | 36.83 |
| Ex. 7 | $CH_2Cl_2$ | $CH_3CN$ | bubbling | bl.tar | 25.80 | 60.40 |
| Ex. 8 | ether | $CH_2Cl_2$ | bubbling | bl.tar | 14.80 | 32.43 |
| Ex. 9 | ether | $CH_3CN$ | bubbling | bl.tar | 18.70 | 41.91 |
| Ex. 10 | ether | $CH_2Cl_2$ | pressure | bl.tar | 0.55 | 1.08 |

Yield based on purity by GLC analysis.
*Isolated crude yield.

TABLE 2

Comparison of Present Invention (Ex. 14) vs. Prior Art Process (Ex. 11–13) for Preparing (1-Methylcyclohexyl)methane Sulfamate

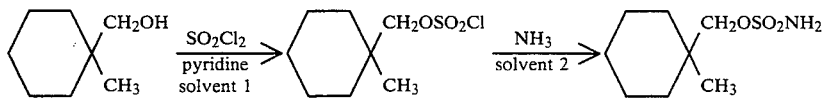

| Process | solvent 1 | solvent 2 | $NH_3$ | Phys. Descript | Purity (%) | Yield # |
|---|---|---|---|---|---|---|
| Ex. 11 | $CH_2Cl_2$ | $CH_3CN$ | bubbling | bl.tar | 2.24 | 1.34 |
| Ex. 12 | ether | $CH_3CN$ | bubbling | bl.tar | 0.00 | 0.00 |
| Ex. 13 | $CH_2Cl_2$ | $CH_2Cl_2$ | bubbling | bl.tar | 29.10 | 23.97 |
| Ex. 14 | toluene | THF | 28 psi | yel.oil | 95.00 | 81.33 |

Yield based on purity by GLC analysis.

Example 1

Preparation of 2,3:4,5-bis-O-(1-methylethylidene)-β-D-fructopyranose

Under nitrogen, acetone (144.0 L, 113.0 kg, 1946 mol) was cooled to 0°–10° C. With stirring, concentrated sulfuric acid (7.2 L, 13.2 kg, 135.6 mol) was added gradually (approx. 0.5 h) so that the temperature did not exceed 20° C. (jacket temperature at −15° C.). External cooling was discontinued and D-fructose (12.0 kg, 66.6 mol) was added gradually (in 2.0 kg portions) over 2 h while maintaining the temperature between 8°–15° C. The suspension was stirred at room temperature for an additional 2–3 h after all the fructose had dissolved. The solution was then cooled to 5° C. and 50% sodium hydroxide (24.0 kg, 297.6 mol) was added at a rate so as to maintain the solution temperature below 20° C. (addition was complete in 1 h with a jacket temperature at ether (48.8 kg, 66.4 L). The solution was washed with distilled water (2×9.0 L) and concentrated to give an oil. The oil was dissolved in hexane (24.0 L)/isopropanol (3.5 L) with gradual warming to 60° C. The product crystallized with cooling. The solid was collected by centrifugation and dried in a vacuum oven at 38° C. for 8.0 h to give 10.8 kg (62.4% yield, 100.8% purity by GLC) of a white solid, mp 95°–96° C.

Example 2

Preparation of 2,3:4,5-bis-O-(1-methylethylidene)-β-D-fructopyranose sulfonyl chloride (chlorosulfate)

A solution of sulfuryl chloride (486.9 g, 3.60 mol) and toluene (4.0 L) was cooled to −10° C. A solution of the alcohol of Example 1 (782.4 g, 3.00 mol) and pyridine (285.3 g, 3.60 mol) in toluene (4.0 L) was added to the cooled sulfuryl chloride solution. The rate of addition was regulated so that the reaction temperature was maintained between −10° to 5° C. (required 1.5 h). A white solid precipitated from the reaction immediately. After the addition was complete, the cooling bath was removed and the mixture stirred for 2.0 h. The reaction mixture was diluted with distilled water (4.0 L) and the resultant layers separated. The organic layer was then washed sequentially with a 10% citric acid solution (2.6 L), distilled water (2.6 L), a saturated sodium bicarbonate solution (2.6 L), and a saturated sodium chloride solution (2.6 L). Removal of the solvent by vacuum distillation (in a 45° C. bath at <5 mm) afforded chlorosulfate (1101 g, 102.2%) as an almost colorless oil. The product was found to be 98.3% pure (wt % by GLC) giving a corrected yield of 100.5%.

Example 3

Preparation of 2,3:4,5-bis-O-(1-methylethylidene) β-D-fructopyranose sulfamate (ammonolysis at 30 psi)

Chlorosulfate (1076.4 g, 3.0 mol) of Example 2 in tetrahydrofuran (8.0 L) was added to a 12.0 L stainless steel autoclave. The autoclave was then pressurized with anhydrous ammonia to 30 psi and stirred (400 rpm) at ambient temperature for 24.0 h. A mild exotherm was noticed after 2.0 h (25° to 38° C.). The autoclave was depressurized by venting to the air. The light yellow solution, containing a white granular solid, was filtered and the filter cake washed with tetrahydrofuran (400 mL). The tetrahydrofuran was removed in vacuo (50° C., house vac) to afford the product as a light yellow oil (1110.0 g, 109.0%). The oil was slurried in n-hexane (2.1 L) and warmed on a steam bath for 0.5 h. The oil changed to a white paste and then crystallized. After cooling to room temperature, the title compound was collected by filtration and air dried for 24.0 h (955.1 g, 93.8% yield and 99.7% pure by GLC giving a corrected yield of 93.5%).

A sample (900 g) was recrystallized from 95% ethanol (900 mL) with the addition of distilled water (1800 mL) and the pH adjusted to 8–8.5 by adding 50% NaOH (3.5 mL). The solid was collected by vacuum filtration and air dried (72.0 h) to yield the title compound (828.0 g, 92.0% isolated yield, 100.1% pure by GLC) as a white solid, mp 123°–124° C.

Example 4

Preparation of 2,3:4,5-bis-O-(1-methylethylidene) β-D-fructopyranose sulfamate (ammonolysis by bubbling ammonia gas)

Into a 500 mL, four-neck round bottom flask equipped with an overhead stirrer, bubbler, thermometer, and inlet tube was placed 19.90 g (0.0556 mol) of the chlorosulfate of Example 2 which was dissolved in 200 mL of tetrahydrofuran. Anhydrous ammonia was bubbled into the solution at room temperature for about 5 h. The reaction mixture was filtered to remove the precipitate and the solvent removed in vacuo. The oil was slurried in hexane (50 mL) with warming on a steam bath until it became pasty white. The oil crystallized with stirring on cooling to room temperature. The mixture was left to stand at room temperature overnight. The mixture was then filtered, washed with hexane, and air dried to give the title compound as a white solid (17.11 g, 96.2% pure by GLC, 87.2% yield).

Example 5

Preparation of 2,3:4,5-bis-O-(1-methylethylidene)-β-D-fructopyranose sulfamate (saturation ammonolysis)

Anhydrous ammonia was added to 490 kg of THF until a pressure of 22 psi was reached. While maintaining a pressure of 22 psi, a solution of the chlorosulfate (303 kg, 845 mol) prepared as in example 2, and dissolved in 415 kg of THF was pumped into the presaturated NH$_3$/THF solution over a 2 h period while maintaining an internal temperature of 15°–20° C. After 3 h the excess ammonia was vented and the reaction mixture filtered. The THF solution was concentrated in vacuo to a syrup, diluted with isopropanol (185 kg), and concentrated again. The resultant residue was dissolved in a solution of isopropanol (150 kg) and petroleum spirits (370 kg) containing 8.0 kg of activated charcoal and warmed to 80° C. for 30 min. The warm solution was filtered to remove charcoal and cooled. After cooling to 0°–5° C., the title compound was collected by filtration and dried under vacuum at 45° C. (239 kg, 83.3% yield).

Example 6—(Comparative Example)

Preparation of 2,3:4,5-bis-O-(1-methylethylidene)-β-D-fructopyranose sulfamate

Under nitrogen, a solution of the alcohol of Example 1 (15.0 g, 0.0576 mol) and pyridine (15 mL, 0.18 mol) in methylene chloride (60 mL) was cooled to −40° C. in a dry ice/isopropanol bath. With stirring, a solution of sulfuryl chloride (16.0 g, 0.118 mol) in methylene chloride (10 mL) was added gradually (approx. 50 minutes) so that the temperature did not exceed −25° C. The ice bath was removed as soon as the addition was complete and the reaction mixture stirred for an additional 2 h. During this time the light yellow precipitate became a clumpy brown solid. Solvent was removed in vacuo to yield a sticky, brown residue. The residue was dissolved in 100 mL methylene chloride and anhydrous ammonia was bubbled through the mixture overnight at ambient temperature. The dark reaction mixture was concentrated in vacuo to give 47.7 g of the title compound as a black residue. The crude product was found to be 15.10% pure by GLC giving a corrected yield of 36.83 %.

Example 7—(Comparative Example)

Preparation of 2,3:4,5-bis-O-(1-methylethylidene)-β-D-fructopyranose sulfamate

The reaction was carried out the same as in Example 6 except acetonitrile was used as the second solvent instead of methylene chloride. The title compound was isolated as a black residue (45.77 g). The crude product was found to be 25.8% pure by GLC giving a corrected yield of 60.40%.

Example 8—(Comparative Example) Preparation of 2,3:4,5-bis-O-(1-methylethylidene)-β-D-fructopyranose sulfamate The reaction was carried out the same as in Example 6 except ether was used instead of methylene chloride in the first step. The title compound was isolated as a black residue (42.84 g). The crude product was found to be 14.8% pure by GLC giving a corrected yield of 32.43%.

Example 9—(Comparative Example)

Preparation of 2,3:4,5-bis-O-(1-methylethylidene)-β-D-fructopyranose sulfamate

The reaction was carried out the same as in Example 6 except ether was used instead of solvent 1 (methylene chloride) and acetonitrile was used instead of methylene chloride for solvent 2 (see Table 1). A black residue (43.82 g) was obtained on work-up. The crude product was found to be 18.70% pure by GLC giving a corrected yield of 41.91%.

Example 10—(Comparative Example)

Preparation of 2,3:4,5-bis-O-(1-methylethylidene)-β-D-fructopyranose sulfamate

The reaction was carried out the same as in Example 8 except that the chlorosulfate/methylene chloride solution was placed in a pear shaped pressure bottle and cooled in a dry ice/isopropanol bath. Anhydrous ammonia was bubbled through the mixture for approximately 30 minutes; then the bottle was tightly stoppered and allowed to slowly warm to room temperature overnight. The bottle was cooled back down before opening and the mixture concentrated in vacuo to give 38.51 g of the title compound as a brown tar. The crude product was found to be only 0.55% pure by GLC giving a corrected yield of 1.08%.

Example 11—(Comparative Example)

Preparation of (1-methylcyclohexyl)methane sulfamate

Under nitrogen, a solution of (1-methylcyclohexane)-methanol (7.4 g, 0.057 mol) and pyridine (15 mL, 0.179 mol) in methylene chloride (100 mL) was cooled to −10° C. in a ice/methanol bath. With stirring, a solution of sulfuryl chloride (16.0 g, 0.118 mol) in methylene chloride (20 mL) was added gradually (approx. 1.0 h) so that the temperature did not exceed −5° C. The ice bath was removed and the light yellow solution allowed to slowly warm to room temperature over a 2.0 h period. Solvent was removed in vacuo and the resulting yellow slush was slurried in acetonitrile (140 mL). Anhydrous ammonia was bubbled through the mixture for 4.0 h. The mixture was filtered, washed with fresh acetonitrile, and concentrated in vacuo to give the title compound (7.12 g) as a dark oil. The crude product was found to be only 2.24% pure by GLC giving a corrected yield of 1.34%.

Example 12—(Comparative Example)

Preparation of (1-methylcyclohexyl)methane sulfamate

The reaction was carried out the same as that in Example 11 except diethylether was used for methylene chloride as solvent 1. (see Table 2). No product was isolated based on GLC analysis.

Example 13—(Comparative Example)

Preparation of (1-methylcyclohexyl)methane sulfamate

The reaction was carried out the same as that in Example 11 except methylene chloride was used instead of acetonitrile as solvent 2 (see Table 2). A product (9.85 g) was isolated as a dark oil. The crude product was found to be 29.1% pure by GLC giving a corrected yield of 23.97%.

Example 14

Preparation of (1-methylcyclohexyl)methane sulfamate

Under argon, sulfuryl chloride (18.67 g, 0.138 mol) in toluene (150 mL) was cooled to −50° C. in a dry ice/acetone bath. With stirring, a solution of 1-methyl-1-cyclohexane methanol (14.74 g, 0.115 mol) and pyridine (10.94 g, 0.138 mol) in toluene (150 mL) was added gradually (approx. 40–50 minutes) so that the temperature did not exceed −45° C. The ice bath was removed as soon as the addition was complete. After stirring for an additional 30 minutes water (300 mL) was added and the layers separated. The organic layer was washed with 10% citric acid (2×60 mL), water (2×100 mL), saturated sodium bicarbonate (1×100 mL), and saturated sodium chloride (1×200 mL), then dried over solid sodium sulfate, filtered, and concentrated in vacuo to give the chlorosulfate (23.53 g, 90.6% yield) as a brownish yellow oil. The oil was dissolved in tetrahydrofuran (300 mL) and the solution added to a 1.0 L autoclave (with glass liner). The autoclave was pressurized with anhydrous ammonia to 28 psi and stirred (290 rpm) at ambient temperature for 16 h. A mild exotherm was noticed after 1.0 h (22°–35° C.). The autoclave was depressurized by venting to the air. The mixture was filtered and the solvent removed in vacuo to give 20.41 g of the title compound as a yellow oil. The product was found to be 95.0% pure by GLC giving a corrected yield of 81.33%.

Examples 15–18—Comparative Examples

In these examples sulfamates were prepared using the process of the present invention (i.e., Ex. 3) but limiting the choice of solvents to those disclosed by Maryanoff, B. E. et. al. in U.S. Pat. No. 4,582,916. The results obtained in these comparative examples are disclosed in Table 3 below.

TABLE 3

Comparison of Present Invention (Ex. 3) vs. Prior Art Solvents (Ex. 15–18) for Preparing Sulfamate VII

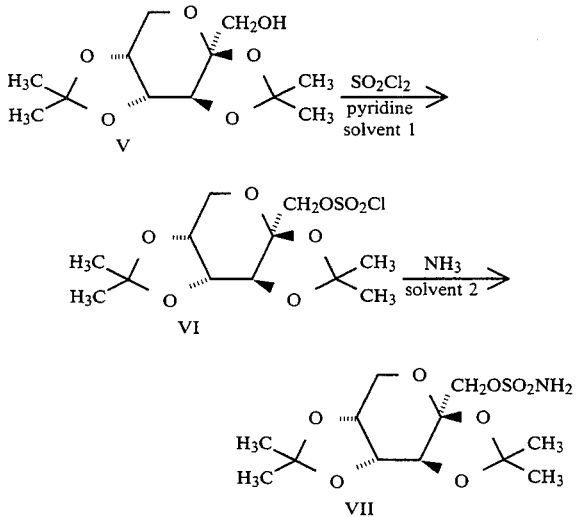

| Process | solvent 1 | solvent 2 | NH$_3$ | Purity (%) (VII) | Yield # (VII) |
|---|---|---|---|---|---|
| Ex. 3 | toluene | THF | 30 psi | 99.70 | 93.50 |
| Ex. 15 | CH$_2$Cl$_2$ | CH$_2$Cl$_2$ | 30 psi | 96.76 | 87.08 |

TABLE 3-continued

| Ex. 16 | CH$_2$Cl$_2$ | CH$_3$CN | 30 psi | 93.19 | 77.95 |
| Ex. 17 | ether | CH$_2$Cl$_2$ | 30 psi | 96.20 | 83.85 |
| Ex. 18 | ether | CH$_2$CN | 30 psi | 94.09 | 77.60 |

A comparison of the examples of the present invention (Exs. 3–5 and 14) versus those comparative examples of the prior art (Exs. 6–13) in Tables 1 and 2 evidences the advantages of the use of the particularly selected solvents of the process of the present invention to produce surprisingly superior results over the prior art processes. A direct comparison of Ex. 4 of the invention utilizing the preferred solvents of the invention, e.g. toluene and THF versus comparitive prior art Exs. 6–9 in Table 1 shows a yield improvement of at least 40% and a significant purity improvement for the final product 2,3:4,5-bis-O-(1-methylethylidene)-β-D-fructopyranose sulfamate. Analagous process result improvements are illustrated in Table 2 for the preparation of (1-methylcyclohexyl)methane sulfamate.

Table 3 illustrates not only the importance of solvent selection but also the importance of stabilization of the chlorosulfate intermediate to contribute to improved yields obtainable by the process of the invention as compared to the prior art. For example, comparing Ex. 10 (Table 1) of the prior art with Ex. 17 (Table 3) of the invention, whereby, both use the same prior art solvents, but Ex. 17 provides the additional step of stabilizing the chlorosulfate intermediate, reveals significant improvement in yield and purity for Ex. 17.

The scope of the present invention is not limited by the description, examples and suggested uses described herein and modifications can be made without departing from the spirit of the invention. For example, other sulfamates may be produced utilizing the process of the invention beyond those exemplified herein.

Applications of the process and methods of the present invention can be accomplished by any synthetic method and technique as is presently or prospectively known to those skilled in the chemical and pharmaceutical process arts. Thus it is intended that the present invention cover any modifications and variations of this invention provided that they come within the scope of the appended claims and their equivalents.

What is claimed is:

1. A two step process for synthesizing sulfamates of the formula I:

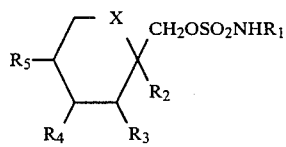

wherein X is CH$_2$ or oxygen;
R$_1$ is hydrogen or C$_1$–C$_4$ alkyl; and
R$_2$, R$_3$, R$_4$ and R$_5$ are independently hydrogen or alkyl, and, when X is oxygen, any of R$_2$ and R$_3$, or R$_4$ and R$_5$, together, may be a methylenedioxy group of the formula (IV):

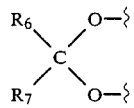

wherein R$_6$ and R$_7$ are the same or different and are hydrogen, alkyl or are alkyl joined together to form a cyclopentyl or cyclohexyl ring, with the proviso that R$_6$ and R$_7$ may not both be H at the same time; the process comprising in a first step, reacting an alcohol of the formula RCH$_2$OH, wherein R is a moiety of the formula II:

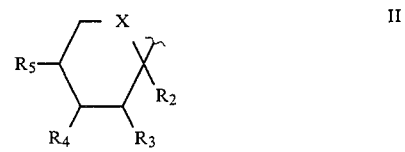

with sulfuryl chloride in the presence of a base selected from the consisting of pyridine, pyridine derivatives and triethylamine in a solvent of toluene to form a chlorosulfate compound of the formula III: RCH$_2$OSO$_2$Cl; and in a second step reacting the chlorosulfate compound of formula III with an amine of the formula R$_1$NH$_2$ in a solvent of tetrahydrofuran to produce the sulfamate of formula I.

2. The process of claim 1, wherein the amine base is pyridine.

3. The process of claim 1, wherein in the first step the reaction of the compound of the formula RCH$_2$OH with sulfuryl chloride is carried out at a temperature of about −78° C. to 40° C.

4. The process of claim 3, wherein the reaction is carried out at a temperature of from −10° C. to 5° C.

5. The process of claim 1, wherein in the second step the reaction of the compound of the formula III with an amine of the formula R$_1$NH$_2$ is carried out at a temperature of about −50° C. to 50° C.

6. The process of claim 5, wherein the temperature is about 15° C. to 20° C.

7. The process of claim 1, further comprising the step of recrystallizing the compound of formula I.

8. The process of claim 7, wherein the recrystallization step is carried out using a recrystallization medium selected from either of alcohol and water, or ethylacetate/hexane.

9. The process of claim 1, wherein said sulfamate is 2,3:4,5-bis-O-(1-methylethylidene)-β-D-fructopyranose sulfamate.

10. The process of claim 1, wherein said sulfamate is 2,3:4,5-bis-O-(1-methylethylidene)-β-L-fructopyranose sulfamate.

11. The process of claim 1, wherein said sulfamate is (1-methylcyclohexyl)methane sulfamate.

12. The process of claim 1, wherein in the second step the reaction of the compound of formula III with an amine of formula R$_1$NH$_2$ is carried out at a pressure of from about one atmosphere to 50 psi.

13. The process of claim 12, wherein the pressure is about 30 psi.

14. The process of claim 12, wherein the pressure is about 22 psi.

15. The process of claim 1, wherein in the second step the reaction of the compound of the formula III with an amine of the formula $R_1NH_2$ is carried out in a presaturated solution of the amine.

16. The process of claim 15, wherein the amine of the formula $R_1NH_2$ is ammonia.

17. The process of claim 1, wherein in the second step the reaction of the compound of formula III with an amine of the formula $R_1NH_2$ is carried out by bubbling the amine into a solution containing the compound of formula III.

18. The process of claim 17 wherein the amine of the formula $R_1NH_2$ is ammonia.

19. The process of claim 1 wherein said compound of formula III is 2,3:4,5-bis-O-(1-methylethylidene)-β-D-fructopyranose sulfonyl chloride.

20. The process of claim 1 wherein said compound of formula III is 2,3:4,5-bis-O-(1-methylethylidene)-β-L-fructopyranose sulfonyl chloride.

21. The process of claim 1 wherein the chlorosulfate compound of formula III is stabilized by an aqueous wash or treatment with a base prior to its reacting in the second step of the process.

22. The process of claim 21 wherein the chlorosulfate is stabilized by an aqueous wash.

23. A two step process for synthesizing sulfamates of the formula VII:

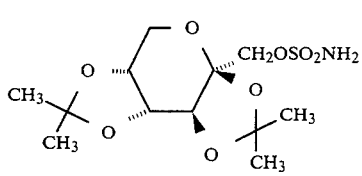

comprising in a first step reacting a compound of formula V:

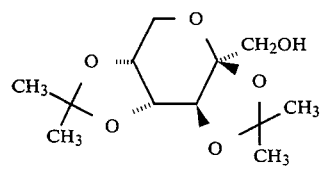

with sulfuryl chloride in a toluene solvent in the presence of pyridine at a temperature of about −10° C. to 5° C. to produce a compound of the formula VI:

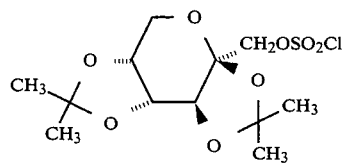

and thereafter in a second step reacting the compound of formula VI with gaseous ammonia at a pressure of about 14 to 30 psi in tetrahydrofuran to produce the compound of formula VII, and thereafter recrystallizing the compound of formula VII from an ethanol and water solvent.

24. The process of claim 23, wherein in the second step the compound of Formula IV is reacted with ammonia at a temperature of about 15° to 20° C.

25. The process of claim 30 wherein the chlorosulfate compound of formula VI is stabilized by an aqueous wash and treatment with a base prior to its reacting in the second step of the process.

26. A two step process for synthesizing sulfamates of the formula VII:

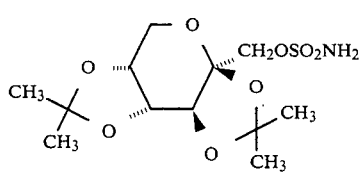

comprising in a first step reacting a compound of formula V:

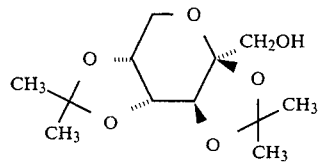

with sulfuryl chloride in a toluene solvent in the presence of pyridine at a temperature of about −10° C. to 5° C. to produce a chlorosulfate compound of the formula VI:

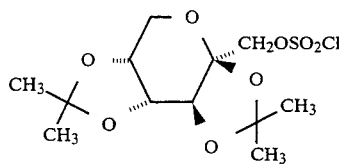

the chlorosulfate compound of formula VI is then stabilized by aqueous wash or treatment with a base; and thereafter in a second step reacting the compound of formula VI with gaseous ammonia at a pressure or about 14 to 30 psi in tetrahydrofuran to produce the compound of formula VII, and thereafter recrystallizing the compound of formula VII from an ethanol and water solvent.

27. The process of claim 26 wherein the chlorosulfate is stabilized by an aqueous wash.

28. The process of claim 26, wherein in the second step the compound of Formula VI is reacted with ammonia at a temperature of about 15° to 20° C.

* * * * *